United States Patent [19]
Cutie

[11] Patent Number: 5,891,419
[45] Date of Patent: Apr. 6, 1999

[54] ENVIRONMENTALLY SAFE FLUNISOLIDE AEROSOL FORMULATIONS FOR ORAL INHALATION

[75] Inventor: Anthony J. Cutie, Bridgewater, N.J.

[73] Assignee: Aeropharm Technology Limited, Edison, N.J.

[21] Appl. No.: 840,577

[22] Filed: Apr. 21, 1997

[51] Int. Cl.$^6$ ....................................................... A61K 9/12
[52] U.S. Cl. ................................ 424/46; 424/45; 514/826
[58] Field of Search ......................... 424/45, 46; 514/826

[56] References Cited

U.S. PATENT DOCUMENTS

| | | |
|---|---|---|
| 2,868,691 | 1/1959 | Porush et al. . |
| 2,885,427 | 5/1959 | Ruh et al. . |
| 3,261,748 | 7/1966 | Larsen . |
| 4,129,603 | 12/1978 | Bell . |
| 4,174,295 | 11/1979 | Bargigia et al. . |
| 5,126,123 | 6/1992 | Johnson . |
| 5,182,097 | 1/1993 | Byron et al. . |
| 5,190,029 | 3/1993 | Byron et al. . |
| 5,225,183 | 7/1993 | Purewal et al. . |
| 5,254,330 | 10/1993 | Ganderton et al. . |
| 5,376,386 | 12/1994 | Ganderton et al. . |
| 5,439,670 | 8/1995 | Purewal et al. . |
| 5,474,759 | 12/1995 | Fassberg et al. . |
| 5,492,688 | 2/1996 | Byron et al. . |
| 5,569,450 | 10/1996 | Duan et al. . |
| 5,605,674 | 2/1997 | Purewal et al. . |
| 5,607,662 | 3/1997 | Baskeyfield et al. . |
| 5,653,962 | 8/1997 | Akehurst et al. . |
| 5,658,549 | 8/1997 | Akehurst et al. . |
| 5,674,471 | 10/1997 | Akehurst et al. . |
| 5,674,472 | 10/1997 | Akehurst et al. . |
| 5,676,929 | 10/1997 | Akehurst et al. . |
| 5,676,931 | 10/1997 | Adjei et al. . |
| 5,683,676 | 11/1997 | Akehurst et al. . |
| 5,683,677 | 11/1997 | Purewal et al. . |
| 5,688,782 | 11/1997 | Neale et al. . |
| 5,695,743 | 12/1997 | Purewal et al. . |
| 5,720,940 | 2/1998 | Purewal et al. . |
| 5,725,841 | 3/1998 | Duan et al. . |
| 5,736,124 | 4/1998 | Akehurst et al. . |
| 5,744,123 | 4/1998 | Akehurst et al. . |

FOREIGN PATENT DOCUMENTS

| | | |
|---|---|---|
| 2046093 | 11/1980 | United Kingdom . |
| 93/11745 | 4/1992 | WIPO . |
| 92/22287 | 8/1992 | WIPO . |
| 95/17195 | 11/1994 | WIPO . |

OTHER PUBLICATIONS

Saunders, "Handbook of Aerosol Technology" 2nd ed. pp. 30–35, 166–167, and 232–233, Von Nostrand Reinhold Co. (1979).

DuPont Update "Fluorocarbon/Ozone", published by DuPont, Willington, DE (Mar. 1987).

Dictionnaire Vidal, 55th ed. pp. 547–548, O.V.P. Paris (1979).

M. Jones, New Scientist, pp. 56–59, May 26, 1988.

Manufacturing Chemist, p. 3, Jun. 1988.

Organic Chemicals Department, E.I. Du Pont de Nemocers & Co., Research Disclosure, p. 70, Oct. 1977.

H.O. Spauschus, Rev. Int. Froid., vol. 11, pp. 389–392 (1988).

D.R. Strobach, Aerosol Age, pp. 32–43 (1988).

*Primary Examiner*—Raj Bawa
*Attorney, Agent, or Firm*—Frommer Lawrence & Haug LLP

[57] ABSTRACT

Aerosol formulations for oral inhalation containing flunisolide dispersed in HFC 134a and/or HFC 227 which are free of chlorofluorocarbons and surfactants, and contain little or no ethanol, are disclosed. Metered dose inhalers suitable for delivering such formulations are also disclosed.

14 Claims, No Drawings

ENVIRONMENTALLY SAFE FLUNISOLIDE AEROSOL FORMULATIONS FOR ORAL INHALATION

FIELD OF THE INVENTION

This invention relates to flunisolide aerosol ormulations for oral inhalation and, more particularly, to such formulations which are free of chlorofluorocarbons and surfactants and contain little or no ethanol.

BACKGROUND OF THE INVENTION

Drugs for treating respiratory disorders are frequently administered in oral aerosol formulations. One widely used method for dispensing such an aerosol drug formulation involves making a formulation of the drug in a liquified gas known as a propellant. The drug may be dissolved or suspended in the propellant, or in a combination slurry-solution.

The formulation is dispensed by actuation of a dose metering valve affixed to the container the valve being designed to consistently release a fixed, predetermined amount of the drug formulation upon each activation. As the formulation is forced from the container through the dose metering valve by the high vapor pressure of the propellant, the propellant rapidly vaporizes, leaving a fast-moving cloud of very fine particles or droplets of the drug formulation. This cloud is then directed into the mouth of the patient. Concurrently with the activation of the aerosol dose metering valve, the patient inhales the drug formulation particles into the lungs. Systems for dispensing drugs in this way are known as metered dose inhalers (MDIs).

Chlorofluorocarbons (CFCs) have been used extensively as propellants in drug formulations that are delivered to patients via an MDI. However, recent scientific evidence suggests that CFCs damage the Earth's ozone layer. It is believed that ozone blocks harmful ultraviolet rays and that depletion of the ozone layer will result in the incidence of skin cancer. As a result, steps have been taken to reduce CFC production and usage, and recent recommendations have been made that CFC production be virtually discontinued by the end of this century. Until recently, however, few propellant systems have been discovered which are suitable alternatives to the use of CFCs in MDIs.

The nonchlorinated propellants 1,1,1,2-tetrafluoroethane, also known as hydrofluorocarbon (HFC) 134a, and 1,1,1,2,3,3,3-heptafluoropropane, also known as HFC 227, are among the leading candidates for replacement of the ozone-damaging CFC propellants. However, the substitution of a non-CFC propellant for the CFC propellants in MDI formulations is not straightforward. There are drug solubility, drug stability and deliverability problems as well as particle size issues which must be addressed when substituting propellants in an MDI formulation. MDIs contain drugs which are dissolved or suspended as micronized particles, propellants in the form of liquified gases, and surface active compounds, or "surfactants," of a type and in a concentration suitable for suspension or dissolution of the drug. Surfactants are included in the formulation to improve particle dispersibility, prevent deaggregation and improve valve function by virtue of its lubricating properties. In some solution formulations, a co-solvent may be added to enhance drug dissolution, although this practice may have the disadvantage of decreasing the fraction of the metered dose which may be inhaled and contributing to particle size growth.

HFC 134a, or 1,1,1,2-tetrafluoroethane (the names will be used interchangeably herein) is nonflammable, has low toxicity and has vapor pressure suitable for use in aerosols. However, HFC 134a is a very poor solvent which fails to dissolve or adequately disperse commonly used surfactants such as sorbitan trioleate, sorbitan monooleate, lecithins and oleic acid in useful concentrations without the aid of a co-solvent.

Similarly, HFC 227, or 1,1,1,2,3,3,3-heptafluropropane (the names will be used interchangeably herein) is nonflammable, has low toxicity and has a vapor pressure suitable for use in aerosols. However, the polarity and solubility of HFC 227 differ from those of commonly used CFC propellants, and many commonly used surfactants are not soluble or are poorly dispersible in HFC 227.

Flunisolide is an anti-inflammatory synthetic fluorinated corticosteroid having the chemical name 6α-fluoro-11β, 16α,17,21-tetrahydroxypregna-1,4-diene-3,20-dionecyclic-16,17-acetal with acetone. Flunisolide is useful for controlling the symptoms of bronchial asthma and in the treatment of seasonal and perennial rhinitis. Presently available flunisolide formulations for MDIs utilize CFCs such as trichloromonofluoromethane, dichlorodifluoromethane and dichlorotetrafluoroethane as propellants. Thus, there remains a need for an environmentally safe flunisolide formulation for MDIs utilizing hydrofluorocarbon propellants such as HFC 134a and HFC 227.

Numerous attempts have been made to formulate aerosols for oral inhalation using non-ozone depleting propellants. However, these formulations generally require the addition of surfactants, polar cosolvents or other adjuvants, and some require the additional manufacturing step of precoating the drug particles with a surfactant prior to dispersal in the propellant.

For example, U.S. Pat. No. 5,225,183 to Purewal et al. discloses MDI formulations which include HFC 134a, a surface active agent, and an adjuvant compound having a higher polarity than HFC 134a. The inclusion of a higher polarity compound in the formulation is said to be critical to the stability and performance of the MDI formulation. The surface active agent is used to stabilize the formulation and lubricate the valve components.

U.S. Pat. No. 5,492,688 to Byron et al. relates to MDI formulations which utilize HFC 134a as the propellant and include a polar surfactant for suspending, solubilizing, wetting and emulsifying the drug constituent and lubricating the valve components of the MDI.

U.S. Pat. No. 5,182,097 to Byron et al. relates to aerosol formulations consisting of 1,1,1,2-tetrafluoroethane, a drug and oleic acid as a surfactant to aid in dispersing the drug in the propellant.

International Application Publication No. W091/04011 relates to medicinal aerosol formulations in which the micronized drug particles are pre-coated with a surfactant prior to dispersal in 1,1,1,2-tetrafluoroethane.

It has now been surprisingly found that HFC 134a and HFC 227 may be used as propellants for medicinal aerosol formulations containing flunisolide without the need for a surfactant and without the need to pre-coat the drug prior to dispersal in the propellant.

SUMMARY OF THE INVENTION

This invention relates to an aerosol formulation which is substantially free of chlorofluorocarbons and surfactants and which comprises a therapeutically effective amount of micronized flunisolide, a propellant selected from the group consisting of HFC 134a, HFC 227 and a mixture thereof and, optionally, ethanol. In a preferred embodiment, flunisolide is present in an amount from about 0.01% to about 2% by weight of the formulation. In a more preferred embodiment, flunisolide is present in an amount from about 0.10% to about 1.5% by weight of the formulation. In a most preferred embodiment, flunisolide is present in an amount from about 0.40% to about 0.90% by weight of the formulation.

Additionally, this invention relates to a method for treating a respiratory disorder in a patient by administering to the patient an effective amount of an aerosol formulation which is substantially free of chlorofluorocarbons and surfactant and which comprises a therapeutically effective amount of micronized flunisolide, a propellant selected from the group consisting of HFC 134a, HFC 227 and a mixture thereof and, optionally, ethanol. In a preferred embodiment, the respiratory disorder is bronchial asthma.

This invention also relates to a metered dose inhaler suitable for delivering an aerosol formulation. The metered dose inhaler comprises a container capable of withstanding the vapor pressure of the propellant used, and an aerosol formulation substantially free of chlorofluorocarbons and surfactants contained in the container. The formulation comprises a therapeutically effective amount of micronized flunisolide and a propellant selected from the group consisting of HFC 134a, HFC 227 and a mixture thereof. The container is closed with a metering valve having a gasket. In a preferred embodiment, the gasket is made from nitrile rubber. In another preferred embodiment, the gasket is made from ethylene-propylene-diene monomers (EPDM) rubber.

DETAILED DESCRIPTION OF THE INVENTION

The present invention provides an aerosol formulation for oral inhalation comprising a therapeutically effective amount of flunisolide dispersed in a propellant comprising a hydro-fluorocarbon selected from the group consisting of 1,1,1,2-tetrafluoroethane, 1,1,1,2,3,3,3-heptafluoropropane, and a mixture thereof. The formulation is substantially free of chlorofluorocarbons and surfactants. Optionally, ethanol may be included in an amount effective to wet and aid in dispersing the flunisolide in the formulation, without dissolving the flunisolide. Such formulations are suitable for the treatment of the symptoms of respiratory disorders, such as bronchial asthma.

For purposes of the present invention the term "substantially free of chlorofluorocarbons and surfactants" is intended to mean containing no significant amounts of chlorofluorocarbons or surfactants, i.e. less than 0.01% by weight of the formulation.

HFC 134a and/or HFC 227 are generally present in the formulations of the present invention in an amount of at least 90% by weight of the formulation, and preferably greater than 95% by weight of the formulation. Most preferably, the propellants are present in an amount from about 98.0% to about 99.75% by weight of the formulation.

The concentration of flunisolide in the formulations of the present invention depends upon the desired dosage, but is generally between about 0.005% and about 5% of the formulation by weight, and preferably comprises from about 0.01% to about 2% by weight of the formulation. More preferably, flunisolide comprises from about 0.10% to about 1.5% by weight of the formulation. Most preferably, flunisolide comprises from about 0.40% to about 0.90% of the formulation.

In formulations of the present invention where ethanol is present, it comprises less than 2% of the formulation. Preferably ethanol is present in an amount from about 0.5% to about 1.5% by weight of the formulation. More preferably, ethanol comprises about 1% or less by weight of the formulation.

Formulations wherein ethanol merely aids in dispersing the drug, such as those described herein, have many advantages over formulations wherein the drug is dissolved in ethanol. Suspensions often provide a smaller and more uniform particle size than solutions, and lend themselves to use with spacer devices better than solutions do. The less ethanol present in the formulation, the less problem there will be with adsorption of the drug onto the valve components, and the smaller the quantity and variety of extractables. In addition, use of little or no ethanol avoids the pharmacological issues raised by the application of large amounts of ethanol to the mucous membranes.

The particle size of the micronized flunisolide should be no greater than 100 microns diameter, since larger particles may clog the valve or orifice of the container. Preferably substantially all of the particles should be less than 25 microns in diameter. More preferably substantially all of the particles should be less than about 10 microns in diameter. Most preferably substantially all of the particles should be from about 0.5 to about 8 microns in diameter. There is no lower limit on particle size except that which will be readily absorbed and retained on or in body tissues. When particles of less than about one-half micron in diameter are administered by inhalation, they tend to be exhaled by the patient.

Flavoring or taste-masking agents optionally may be added to the compositions of the instant invention. Suitable flavoring agents will be known to the skilled artisan. Preferred flavoring agents include menthol and peppermint oil and combinations thereof. The flavoring agent is preferably present in an amount effective to mask the taste of the drug when an aerosolized dose of the formulation is inhaled orally. In general, amounts of about 0.01% to about 5.0% by weight of the composition are used with amounts of about 0.05% to about 1.0% by weight being preferred.

In addition to flavoring agents, other excipients may be added to an aerosol formulation to improve drug delivery, shelf life and patient acceptance. Such optional excipients include, but are not limited to, buffers, antioxidants, dispersing agents and chemical stabilizers. Such excipients must be non-reactive with the drug and relatively non-toxic. The vapor pressure of the excipients should be such that the overall formula vapor pressure should be below 80 psig at room temperature. A preferred excipient is beta-lactose, which is useful as a dispersing agent, stability modifier, density modifier, drug transport facilitator, carrier of additives and respiratory sensitizer or desensitizer.

The formulations of the present invention may be filled into conventional aerosol containers equipped with metering valves using conventional filling equipment well known to those skilled in the art. All of the propellant may be charged to the compounding tank at once, or a portion of the propellant may be charged as part of the concentrate with the remainder being charged as a final step, NEAT.

The aerosol containers are closed with metering valves, which are designed to deliver a metered amount of the formulation per actuation and include a gasket to prevent leakage of the propellant through the valve. The gasket may be made from any suitable elastomeric material. Gaskets made from nitrile rubber and ethylene-propylene-diene monomers (EPDM) rubber have been found to be particularly suitable for use with the formulations of the present invention.

Depending on the particular application the container may be charged with a predetermined quantity of formulation for single or multiple dosing. Typically, the container is sized for multiple-dosing, and, therefore, it is very important that the formulation delivered is substantially uniform for each dosing. Preferably, the container is charged with a sufficient quantity of the formulation for 100–800 mcg flunisolide/actuation for at least 100 actuations.

The chemical and physical stability and the pharmaceutical acceptability of the aerosol formulations of the present invention may be determined by conventional analytical techniques well known to those skilled in the art. These include particle size measurement, drug active total assay, degradation assay, drug delivery per actuation, weight delivery per actuation, component/formulation compatibility and extractables, etc.

The advantages of the present invention can be further appreciated by reference to the following examples. These examples are intended to illustrate preferred embodiments and are by no means intended to limit the effective scope of the claims. All percentages are by weight unless otherwise specified.

| Ingredient | Quantity per Can |
| --- | --- |
| Ethanol, 200 proof | 0.0724 g |
| Flunisolide anhydrous, micronized | 0.0332 g[1] |
| HFC 134a | 7.1300 g |

[1]Includes a 10% overcharge to assure a 250 mcg/actuation delivery from the valve, 120 theoretical actuations to ensure the delivery of 100 metered actuations.

The entire amount of alcohol was charged to a pressure vessel. Mixing of the tank contents was begun, and continued throughout the entire compounding and filling/manufacturing process. While homogenizing the contents of the pressure vessel, the entire amount of drug active was charged to the vessel. The vessel was sealed, cooled to −40° C. and pressurized to 35 psig. When the set point temperature and pressure was achieved, the entire amount of propellant was charged to the compounding tank by way of a precooling heat exchanger set to cool the propellant to −40° C. at the appropriate flow rate. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The full dose was pressure filled through the valve using pressure filling equipment.

| Ingredient | Quantity per Can |
| --- | --- |
| Ethanol, 200 proof | 0.0660 g |
| Flunisolide anhydrous, micronized | 0.0840 g[1] |
| HFC 227 | 8.2800 g |

[1]Includes a 10% overcharge to assure a 500 mcg/actuation delivery from the valve, 120 theoretical actuations to ensure the delivery of 100 metered actuations.

The formula is prepared by the method of Example 1.

| Ingredient | Quantity per Can |
| --- | --- |
| Flunisolide anhydrous, micronized | 0.0330 g[1] |
| HFC 134a | 7.2200 g |

[1]Includes a 10% overcharge to assure a 250 mcg/actuation delivery from the valve, 120 theoretical actuations to ensure the delivery of 100 metered actuations.

A pressure vessel was sealed, cooled to −40° C. and pressurized to 35 psig. When the set point temperature and pressure was achieved, the entire amount of propellant was charged to the compounding tank by way of a precooling heat exchanger set to cool the propellant to −40° C. at the appropriate flow rate. Mixing of the tank contents was begun, and continued throughout the entire compounding and filling/manufacturing process. While homogenizing the contents of the pressure vessel, the entire amount of drug active was charged to the vessel. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The full dose was pressure filled through the valve using pressure filling equipment.

| Ingredient | Quantity per Can |
| --- | --- |
| Flunisolide anhydrous, micronized | 0.0660 g[1] |
| HFC 227 | 8.4000 g |

[1]Includes a 10% overcharge to assure a 500 mcg/actuation delivery from the valve, 120 theoretical actuations to ensure the delivery of 100 metered actuations.

The formula is prepared by the method of Example 3.

| Ingredient | Quantity per Can |
| --- | --- |
| Ethanol, 200 proof | 0.0725 g |
| Flunisolide anhydrous, micronized | 0.0331 g[1] |
| HFC 134a | 3.5700 g[2] |
| HFC 134a | 3.5700 g[3] |

[1]Includes a 10% overcharge to assure a 250 mcg/actuation delivery from the valve, 120 theoretical actuations to ensure the delivery of 100 metered actuations.
[2]50% of the total propellant content charged as part of the concentrate.
[3]50% of the total propellant content charged as a final step, NEAT.

The entire amount of alcohol was charged to a pressure vessel. Mixing of the tank contents was begun, and continued throughout the entire compounding and filling/manufacturing process. While homogenizing the contents of the pressure vessel, the entire amount of drug active was charged to the vessel. The vessel was sealed, cooled to −40° C. and pressurized to 35 psig. When the set point temperature and pressure was achieved, the appropriate amount of propellant was charged to the compounding tank by way of a precooling heat exchanger set to cool the propellant to −40° C. at the appropriate flow rate. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The appropriate concentrate dose was pressure filled through the valve using pressure filling equipment. The balance of the NEAT propellant was then pressure filled to bring the can contents to full weight.

| Ingredient | Quantity per Can |
|---|---|
| Flunisolide anhydrous, micronized | 0.0330 g[1] |
| HFC 134a | 3.6100 g[2] |
| HFC 134a | 3.6100 g[3] |

[1]Includes a 10% overcharge to assure a 250 mcg/actuation delivery from the valve, 120 theoretical actuations to ensure the delivery of 100 metered actuations.
[2]50% of the total propellant content charged as part of the concentrate.
[3]50% of the total propellant content charged as a final step, NEAT.

A pressure vessel was sealed, cooled to −40° C. and pressurized to 35 psig. When the set point temperature and pressure was achieved, the appropriate amount of propellant was charged to the compounding tank by way of a precooling heat exchanger set to cool the propellant to −40° C. at the appropriate flow rate. Mixing of the tank contents was begun, and continued throughout the entire compounding and filling/manufacturing process. While homogenizing the contents of the pressure vessel, the entire amount of drug active was charged to the vessel. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The appropriate concentrate dose was pressure filled through the valve using pressure filling equipment. The balance of the NEAT propellant was then pressure filled to bring the can contents to full weight.

| Ingredient | Quantity per Can |
|---|---|
| Flunisolide anhydrous, micronized | 0.0660 g[1] |
| HFC 134a | 3.9100 g |
| HFC 227 | 3.9100 g |

[1]Includes a 10% overcharge to assure a 500 mcg/actuation delivery from the valve, 120 theoretical actuations to ensure the delivery of 100 metered actuations.

A pressure vessel is sealed, cooled to −40° C. and pressurized to 35 psig. When the set point temperature and pressure is achieved, the entire amount of HFC 134a followed by the entire amount of HFC 227 is charged to the compounding tank by way of a precooling heat exchanger set to cool the propellant to −40° C. at the appropriate flow rate. Mixing of the tank contents is begun, and continues throughout the entire compounding and filling/manufacturing process. While homogenizing the contents of the pressure vessel, the entire amount of drug active is charged to the vessel. The temperature and pressure are then adjusted to −10° C. and 100 psig. When the set point temperature and pressure have been achieved, the vessel contents are homogenized for an additional 10 minutes. The tank contents are then recirculated through a pressure filler and the temperature of the concentrate is allowed to equilibrate with the filling equipment for 10 minutes. A 50 mcl metered dose valve is vacuum sealed onto a 20 mm aluminum can by applying vacuum with a vacuum sealing device, then the valve is crimped onto the can while under vacuum. The full dose is pressure filled through the valve using pressure filling equipment.

| Ingredient | Quantity per Can |
|---|---|
| Ethanol, 200 proof | 0.0723 g |
| Menthol, USP | 0.0072 g |
| Flunisolide anhydrous, micronized | 0.0800 g 0.0330 g[1] |
| HFC 134a | 7.1200 g |

[1]Includes a 10% overcharge to assure a 250 mcg/actuation delivery from the valve, 120 theoretical actuations to ensure the delivery of 100 metered actuations.

The entire amount of alcohol was charged to a pressure vessel. Mixing of the tank contents was begun, and continued throughout the entire compounding and filling/manufacturing process. While homogenizing the contents of the pressure vessel, first the entire amount of menthol and then the entire amount of drug active were charged to the vessel. The vessel was sealed, cooled to −40° C. and pressurized to 35 psig. When the set point temperature and pressure was achieved, the entire amount of propellant was charged to the compounding tank by way of a precooling heat exchanger set to cool the propellant to −40° C. at the appropriate flow rate. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The appropriate concentrate dose is pressure filled through the valve using pressure filling equipment.

| Ingredient | Quantity per Can |
|---|---|
| Ethanol, 200 proof | 0.0723 g |
| Menthol, USP | 0.0072 g |
| Flunisolide anhydrous, micronized | 0.0330 g[1] |
| HFC 134a | 3.5600 g[2] |
| HFC 134a | 3.5600 g[3] |

[1]Includes a 10% overcharge to assure a 250 mcg/actuation delivery from the valve, 120 theoretical actuations to ensure the delivery of 100 metered actuations.
[2]50% of the total propellant content charged as part of the concentrate.
[3]50% of the total propellant content charged as a final step, NEAT.

The entire amount of alcohol was charged to a pressure vessel. Mixing of the tank contents was begun, and continued throughout the entire compounding and filling/manufacturing process. While homogenizing the contents of the pressure vessel, first the entire amount of menthol and then the entire amount of drug active were charged to the vessel. The vessel was sealed, cooled to −40° C. and pressurized to 35 psig. When the set point temperature and pressure were achieved, the appropriate amount of propellant was charged to the compounding tank by way of a precooling heat exchanger set to cool the propellant to −40° C. at the appropriate flow rate. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The appropriate concentrate dose was pressure filled through the valve using pressure filling equipment. The balance of the NEAT propellant was then pressure filled to bring the can contents to full weight.

| Ingredient | Quantity per Can |
|---|---|
| Menthol, USP | 0.0073 g |
| Flunisolide anhydrous, micronized | 0.0330 g[1] |
| HFC 134a | 7.2200 g |

[1]Includes a 10% overcharge to assure a 250 mcg/actuation delivery from the valve, 120 theoretical actuations to ensure the delivery of 100 metered actuations.

A pressure vessel was sealed, cooled to −40° C. and pressurized to 35 psig. When the set point temperature and pressure were achieved, the entire amount of propellant was charged to the compounding tank by way of a precooling heat exchanger set to cool the propellant to −40° C. at the appropriate flow rate. Mixing of the tank contents was begun, and continued throughout the entire compounding and filling/manufacturing process. While homogenizing the contents of the pressure vessel, first the entire amount of the menthol and then the entire amount of drug active were charged to the vessel. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The full dose was pressure filled through the valve using pressure filling equipment.

| Ingredient | Quantity per Can |
|---|---|
| Menthol, USP | 0.0073 g |
| Flunisolide anhydrous, micronized | 0.0330 g[1] |
| HFC 134a | 3.6100 g[2] |
| HFC 134a | 3.6100 g[3] |

[1]Includes a 10% overcharge to assure a 250 mcg/actuation delivery from the valve, 120 theoretical actuations to ensure the delivery of 100 metered actuations.
[2]50% of the total propellant content charged as part of the concentrate.
[3]50% of the total propellant content charged as a final step, NEAT.

A pressure vessel was sealed, cooled to −40° C. and pressurized to 35 psig. When the set point temperature and pressure were achieved, the appropriate amount of propellant was charged to the compounding tank by way of a precooling heat exchanger set to cool the propellant to −40° C. at the appropriate flow rate. Mixing of the tank contents was begun, and continued throughout the entire compounding and filling/manufacturing process. While homogenizing the contents of the pressure vessel, first the entire amount of menthol and then the entire amount of drug active were charged to the vessel. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The appropriate concentrate dose was pressure filled through the valve using pressure filling equipment. The balance of the NEAT propellant was then pressure filled to bring the can contents to full weight.

| Ingredient | Quantity per Can |
|---|---|
| Flunisolide anhydrous, micronized | 0.0660 g |
| Menthol USP | 0.0085 g |
| HFC 227 | 8.3900 g[1] |

[1]Includes a 10% overcharge to assure a 500 mcg/actuation delivery from the valve, 120 theoretical actuations to ensure the delivery of 100 metered actuations.

The formula is prepared by the method of Example 10.

| Ingredient | Quantity per Can |
|---|---|
| Flunisolide anhydrous, micronized | 0.0330 g[1] |
| β-lactose | 0.0033 g |
| HFC 134a | 7.2200 g |

[1]Includes a 10% overcharge to assure 500 mcg/actuation delivery from the valve, 120 theoretical actuations to ensure the delivery of 100 metered actuations.

A pressure vessel was sealed, cooled to −40° C. and pressurized to 35 psig. When the set point temperature and pressure was achieved, the entire amount of propellant was charged to the compounding tank by way of a precooling heat exchanger set to cool the propellant to −40° C. at the appropriate flow rate. Mixing of the tank contents was begun, and continued throughout the entire compounding and filling/manufacturing process. While homogenizing the contents of the pressure vessel, first the entire amount of δ-lactose and then the entire amount of drug active were charged to the vessel. The temperature and pressure were then adjusted to −10° C. and 100 psig. When the set point temperature and pressure had been achieved, the vessel contents were homogenized for an additional 10 minutes. The tank contents were then recirculated through a pressure filler and the temperature of the concentrate was allowed to equilibrate with the filling equipment for 10 minutes. A 50 mcl metered dose valve was vacuum sealed onto a 20 mm aluminum can by applying vacuum with a vacuum sealing device, then the valve was crimped onto the can while under vacuum. The full dose was pressure filled through the valve using pressure filling equipment.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. An aerosol formulation consisting of:
   a) a therapeutically effective amount of micronized flunisolide;
   b) a propellant selected from the group consisting of HFC 134a, HFC 227 and a mixture thereof wherein the amount of chlorofluorocarbon is less than 0.01% by weight of the formulation;
   c) less than about 2% to about 0.5% ethanol; and
   d) optionally flavoring or taste-masking agents or excipients.

2. The formulation of claim 1, wherein said flunisolide is present in an amount from about 0.01% to about 2% by weight of the formulation.

3. The formulation of claim 2, wherein said flunisolide is present in an amount from about 0.10% to about 1.5% by weight of the formulation.

4. The formulation of claim 3, wherein said flunisolide is present in an amount from about 0.40% to about 0.90% by weight of the formulation.

5. The formulation of claim 1, wherein said propellant is HFC 134a.

6. The formulation of claim 1, wherein said propellant is HFC 227.

7. The formulation of claim 1, wherein said propellant is a mixture of HFC 134a and HFC 227.

8. The formulation of claim 1, wherein the particle size of said micronized flunisolide is less than about 10 microns.

9. The formulation of claim 5, wherein the particle size of said micronized flunisolide is from about 0.5 to about 5.0 microns.

10. A method for treating a respiratory disorder in a patient comprising the step of administering to a patient in need of such treatment an effective amount of an aerosol formulation according to claim 1.

11. The method according to claim 10, wherein said respiratory disorder is bronchial asthma.

12. A metered dose inhaler suitable for delivering an aerosol formulation which comprises:
    a) a container capable of withstanding the vapor pressure of the propellant used, said container being closed with a metering valve having a gasket; and
    b) an aerosol formulation contained in said container, said formulation consisting of:
       (1) a therapeutically effective amount of micronized flunisolide;
       (2) a propellant selected from the group consisting of HFC 134a, HFC 227 and a mixture thereof wherein the amount of chlorofluorocarbon is less than 0.01% by weight of the formulation;
       (3) less than about 2% to about 0.5% ethanol; and
       (4) optionally flavoring or taste-masking agents or excipients.

13. The metered dose inhaler of claim 12, wherein said gasket is made from nitrite rubber.

14. The metered dose inhaler of claim 12, wherein said gasket is made from ethylene-propylene-diene monomers (EPDM) rubber.

* * * * *

UNITED STATES PATENT AND TRADEMARK OFFICE
CERTIFICATE OF CORRECTION

PATENT NO. : 5,891,419
DATED : April 6, 1999
INVENTOR(S) : Cutie

It is certified that error appears in the above-identified patent and that said Letters Patent is hereby corrected as shown below:

In column 1, line 6 of the Patent, change "ormulations" to --formulations--.
In column 5, line 24 of the Patent, add --Example 1--.
In column 5, line 57 of the Patent, add --Example 2--.
In column 6, line 2 of the Patent, add --Example 3--.
In column 6, line 33 of the Patent, add --Example 4--.
In column 6, line 43 of the Patent, add --Example 5--.
In column 7, line 13 of the Patent, add --Example 6--.
In column 7, line 48 of the Patent, add --Example 7--.
In column 8, line 13 of the Patent, add --Example 8--.
In column 8, line 47 of the Patent, add --Example 9--.
In column 9, line 19 of the Patent, add --Example 10--.
In column 9, line 51 of the Patent, add --Example 11--.
In column 10, line 21 of the Patent, add --Example 12--.
In column 10, line 33 of the Patent, add --Example 13--.
In column 10, line 52 of the Patent, change "6-lactose" to --$\beta$-lactose--.

Signed and Sealed this

Fifth Day of October, 1999

Attest:

Q. TODD DICKINSON

Attesting Officer

Acting Commissioner of Patents and Trademarks